US00PP36348P2

(12) United States Plant Patent
Koot

(10) Patent No.: US PP36,348 P2
(45) Date of Patent: Dec. 31, 2024

(54) ***BUDDLEJA* PLANT NAMED 'Botex 007'**

(50) Latin Name: *Buddleja davidii*
Varietal Denomination: Botex 007

(71) Applicant: Johannes Adrianus Maria Koot, Kaatsheuvel (NL)

(72) Inventor: Johannes Adrianus Maria Koot, Kaatsheuvel (NL)

(73) Assignee: BOTA NIC EXPERIENCE B.V., Kaatsheuvel (NL)

( * ) Notice: Subject to any disclaimer, the term of this patent is extended or adjusted under 35 U.S.C. 154(b) by 0 days.

(21) Appl. No.: 18/665,795

(22) Filed: May 16, 2024

(30) Foreign Application Priority Data

Aug. 16, 2023 (QZ) ..... PBR 20231689

(51) Int. Cl.
*A01H 6/00* (2018.01)
*A01H 5/02* (2018.01)

(52) U.S. Cl.
USPC ..... Plt./242

(58) Field of Classification Search
USPC ..... Plt./242
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Buddleja* plant named 'Botex 007' that is characterized by its dense, very compact and upright plant habit, its flowers that are cherry pink in color, its neat and naturally round plant shape, its very floriferous blooming habit, and its flowers that have a sweet fragrance.

2 Drawing Sheets

Botanical classification: *Buddleja davidii.*
Variety denomination: 'Botex 007'.

BACKGROUND OF THE INVENTION

The present invention relates to a new and distinct cultivar of *Buddleja davidii* and will be referred to hereafter by its cultivar name, 'Botex 007'. 'Botex 007' is a new shrub grown for use as an ornamental landscape plant.

The new cultivar of *Buddleja* is a selection from an ongoing breeding program conducted by the Inventor in Kaatsheuvel, The Netherlands with the goal of creating new cultivars of *Buddleja* with very neat and compact plant habits combined with unique flower colors and floriferous blooming habits.

The Inventor made a cross in July of 2020 between an unnamed and unpatented proprietary plants in the Inventor's breeding program as both the female and male parents. The seeds were pooled from the crosses and therefore the exact parents are unknown. The Inventor selected 'Botex 007' in July of 2021 as a single unique plant amongst the seedlings that resulted from the above cross.

Asexual propagation of the new cultivar was first accomplished by the Inventor using stem cuttings in Kaatsheuvel, The Netherlands in 2021. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Botex 007' as a unique cultivar of *Buddleja.*

1. 'Botex 007' exhibits a dense, very compact and upright plant habit.
2. 'Botex 007' exhibits flowers that are cherry pink in color.
3. 'Botex 007' exhibits a neat and naturally round plant shape.
4. 'Botex 007' exhibits a very floriferous blooming habit.
5. 'Botex 007' exhibits flowers that have a sweet fragrance.

'Botex 007' can be compared to the *Buddleja* cultivars 'Peakeep' (not patented) and 'Botex 005' (U.S. Plant Pat. No. 34,703). 'Peakeep' is similar to 'Botex 007' in having fragrant flowers that are pink in color. 'Peakeep' differs from 'Botex 007' in having a taller plant height, a less narrow plant habit, lighter green foliage, and inflorescences that are less compact, longer and more narrow in shape with flowers that are slightly lighter in color. 'Botex 005' is similar to 'Botex 007' in having a compact and rounded plant habit and very floriferous blooming habit. 'Botex 005' differs from 'Botex 007' in having flowers that are darker pink in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102 (b) (1) for disclosures and/or sales that fall within a one-year grace period to the filing date. Disclosures include but may not be limited to a website listing by Plantipp.

BRIEF DESCRIPTION OF THE DRAWINGS

The accompanying color photographs illustrate the overall appearance and distinct characteristics of the new

*Buddleja*. The photographs were taken of a one-year-old plant as grown in a greenhouse in a 21-cm container in Kaatsheuvel, The Netherlands.

Figure 1:
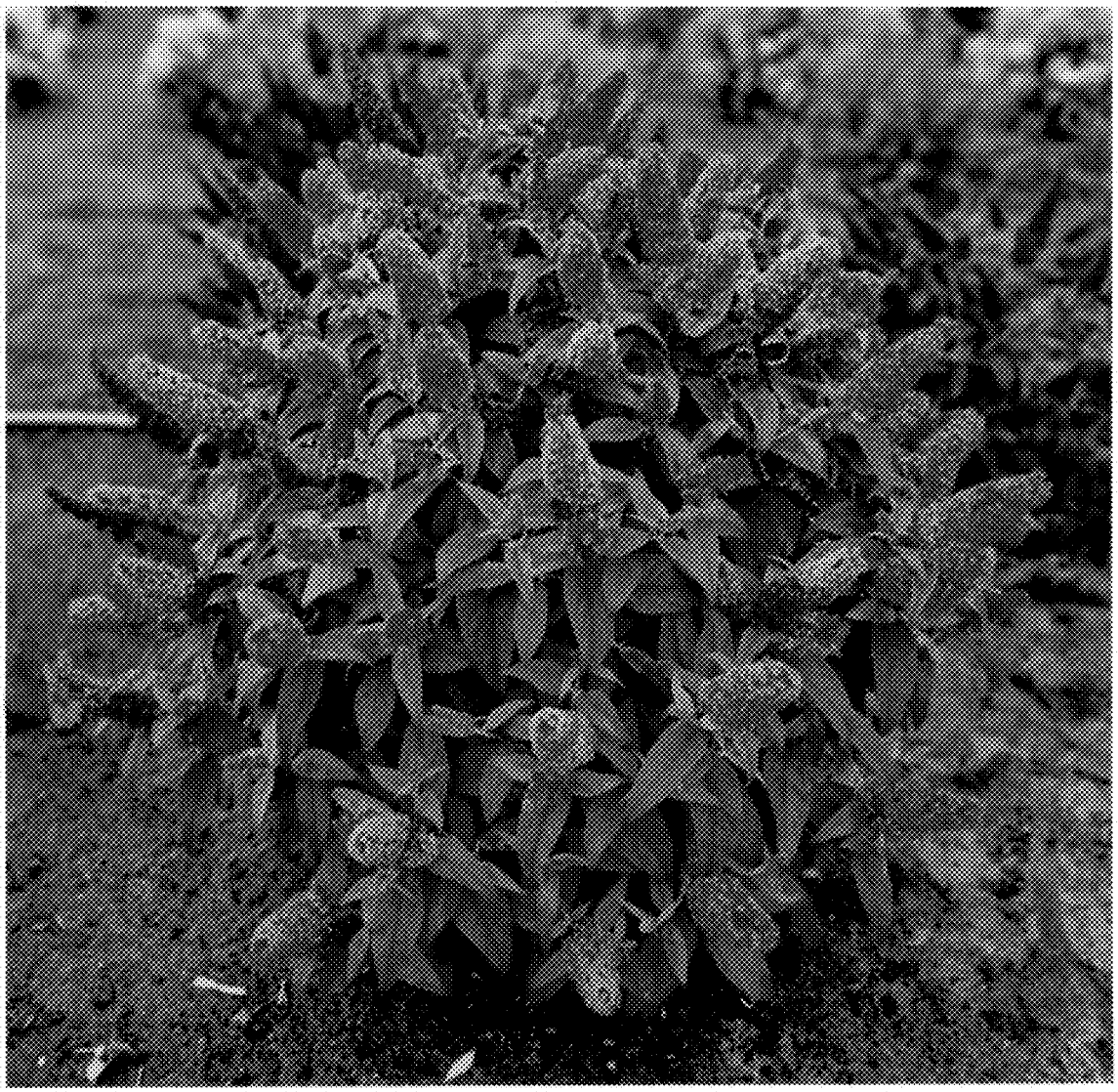

The photograph in FIG. 1 provides a side view of the plant habit of 'Botex 007' in bloom.

Figure 2:
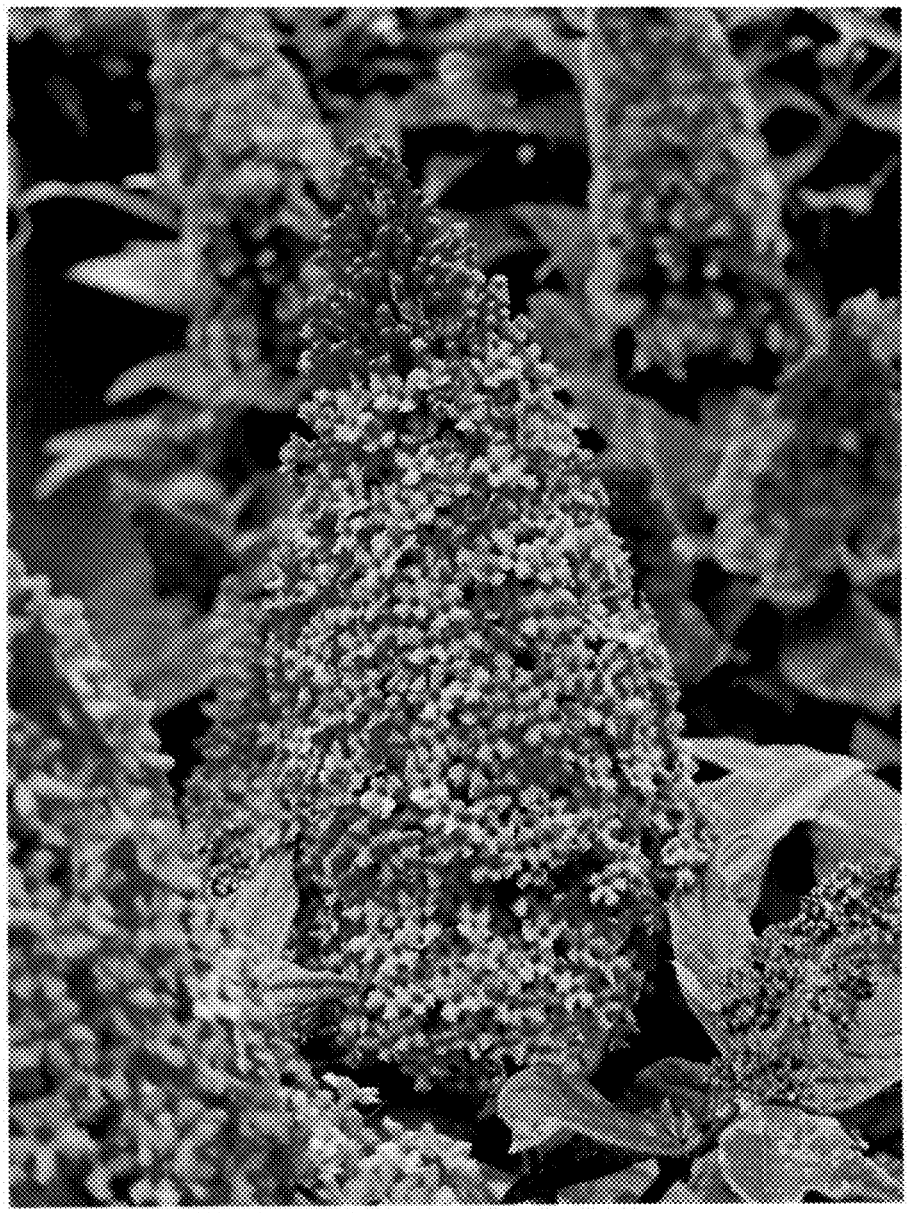

The photograph in FIG. 2 provides a close-up view of an inflorescence of 'Botex 007'.

The colors in the photographs are as close as possible with the photographic and printing technology utilized and the color values cited in the Detailed Botanical Description accurately describe the colors of the new *Buddleja*.

DETAILED BOTANICAL DESCRIPTION

The following is a detailed description of one-year-old plants as grown in a greenhouse in 21-cm containers in Kaatsheuvel, The Netherlands. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

- *Blooming period*.—July to October in The Netherlands.
- *Plant type*.—Deciduous perennial shrub.
- *Plant habit*.—Compact, upright, dense.
- *Plant size*.—An average of 43 cm in height and width as a one-year-old plant grown in a container and an average of 80 cm in height and 85 cm in width as grown in the landscape.
- *Cold hardiness*.—At least in U.S.D.A. Zone 5.
- *Diseases and pests*.—No susceptibility and resistance to diseases or pests has been observed.
- *Propagation*.—Stem cuttings.
- *Root description*.—Fibrous.
- *Root development*.—An average of 8 weeks to initiate roots and eight weeks to fully root as a young plant in a P9 container.
- *Growth rate*.—Vigorous.

Branch description:

- *Branch shape*.—Quadrangular.
- *Branch color*.—Young stems; 145A to 145B, mature stems; 144B with a layer of N187A, old wood 199A to 199B.
- *Branch strength*.—Strong.
- *Branch size*.—An average of 30 cm in length and 7 mm in diameter.
- *Branch surface*.—Pubescent.
- *Branch aspect*.—Held in multiple angles.
- *Branch internode length*.—Average of 4 cm.
- *Branching*.—1 main branch, 2 secondary branches, 6 tertiary.

Foliage description:

- *Leaf shape*.—Narrowly elliptical to elliptical.
- *Leaf division*.—Simple.
- *Leaf base*.—Attenuate.
- *Leaf apex*.—Acute.
- *Leaf fragrance*.—None.
- *Leaf venation*.—Pinnate, color; young upper surface 137C, young lower surface 191B, mature upper surface 145B, mature lower surface 191B, base 145B.
- *Leaf margins*.—Serrate.
- *Leaf arrangement*.—Opposite.
- *Leaf attachment*.—Petiolate.
- *Leaf surface*.—Both sides are smooth, matte, and pubescent.
- *Leaf size*.—An average of 10.5 cm in length and 4.8 cm in width.
- *Leaf quantity*.—8 to 10 per stem.
- *Leaf color*.—Young upper surface; 137C, young lower surface; 191C, mature upper surface; 137A, mature lower surface; 191A to 191B.
- *Petioles*.—An average of 2 mm in length and diameter, medium to high strength, both surfaces 145B in color, both surfaces slightly pubescent.

Inflorescence description:

- *Inflorescence type*.—Compound terminal and axial panicles.
- *Inflorescence size*.—Up to 14 cm in height and 7.3 cm in width.
- *Flower fragrance*.—Sweet, pleasant and medium in strength.
- *Lastingness of flowers*.—An average of 5 days, persistent, inflorescence is semi-indeterminate.
- *Flower buds*.—Oblong, average of 5 mm in length and 1 mm in diameter, 70A to 70B in color.
- *Flower aspect*.—Upright.
- *Flower quantity*.—An average of 150 to 180 flowers per inflorescence.
- *Flower type*.—Single, salverform.
- *Flower surface*.—All surfaces glabrous and smooth.
- *Flower size*.—An average of 1.1 cm in height, 6 mm in diameter, flower throat; 5 mm in length, 1 mm in diameter, flower tube; 3 mm in length, less than 1 mm in diameter.
- *Peduncles*.—An average of 2 cm in length and 2 mm in diameter, 145A in color, strong, glossy and pubescent surface.
- *Pedicels*.—An average of 2 mm in length, 1 mm in diameter, 145B in color, strong, surface is glossy and pubescent.
- *Calyx*.—Campanulate in shape, an average of 2 mm in depth and 1.5 mm in diameter.
- *Sepals*.—4, 1 whorl, rotate arrangement, fused into a campanulate shape, 3 mm in length, 1 mm in width, lanceolate in shape, acute apex, fused base, entire margin, both surfaces are matte and slightly pubescent, color; when opening and fully open upper and lower surface 145A.
- *Petals*.—Average of 4, rotate, fused into salverform, 1 whorl, roughly spathulate in shape, slightly undulate margins, rounded apex, an average of 3 mm in length and width, outer and inner surface is glabrous, velvety and matte, color: upper surface when opening and fully open; margins 70B, center 71C, inside tube 25A, fading to N75B, lower surface 63A.

Reproductive organs:

- *Gynoecium*.—1 pistil, 2 mm in length, style; an average of 1.5 mm in length, 145D in color, stigma; elongated, 1 mm in length and 145B in color, ovary is 145D in color.
- *Androecium*.—Stamens; 4, filament; 4 mm in length and 23B in color, anther; ovate in shape, 1 mm in length, 11D in color, pollen; low in quantity, 11D in color.
- *Fruit and seed*.—No seeds or fruit have been observed to date.

It is claimed:

1. A new and distinct cultivar of *Buddleja* plant named 'Botex 007' as herein illustrated and described.

* * * * *